United States Patent
Baker et al.

(10) Patent No.: US 8,349,780 B2
(45) Date of Patent: Jan. 8, 2013

(54) COMPOSITIONS AND METHODS INCORPORATING PHOTOCATALYSTS

(75) Inventors: Ellen Schmidt Baker, Cincinnati, OH (US); Ioannis Constantine Constantinides, Wyoming, OH (US); Qian Li, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/944,103

(22) Filed: Nov. 11, 2010

(65) Prior Publication Data

US 2011/0114108 A1   May 19, 2011

Related U.S. Application Data

(60) Provisional application No. 61/260,900, filed on Nov. 13, 2009.

(51) Int. Cl.
*C11D 9/36* (2006.01)

(52) U.S. Cl. ........ 510/122; 510/119; 510/130; 510/301; 510/343; 510/372; 510/375; 510/466

(58) Field of Classification Search ............... 510/119, 510/122, 130, 301, 343, 372, 375, 466
See application file for complete search history.

(56) References Cited

U.S. PATENT DOCUMENTS

| | | | |
|---|---|---|---|
| 4,737,445 A | 4/1988 | Frommeld et al. | |
| 4,871,532 A | 10/1989 | Hoogendoorn | |
| 5,300,285 A | 4/1994 | Halloran | |
| 5,906,610 A | 5/1999 | Mehl | |
| 6,283,956 B1 | 9/2001 | McDaniel | |
| 6,989,149 B2 | 1/2006 | Glenn et al. | |
| 8,040,058 B2 | 10/2011 | Douglas et al. | |
| 2002/0139957 A1 | 10/2002 | Matsuo et al. | |
| 2003/0091602 A1 | 5/2003 | Witteler | |
| 2003/0113279 A1 | 6/2003 | Vic | |
| 2004/0043046 A1 | 3/2004 | Vic | |
| 2004/0058855 A1* | 3/2004 | Schwartz et al. | 514/6 |
| 2004/0197285 A1* | 10/2004 | Van Dort | 424/70.12 |
| 2005/0112154 A1 | 5/2005 | Giroud | |
| 2005/0186151 A1 | 8/2005 | Giroud | |
| 2005/0208005 A1 | 9/2005 | Giroud | |
| 2005/0261390 A1 | 11/2005 | Frances | |
| 2006/0110345 A1* | 5/2006 | Lu et al. | 424/64 |
| 2008/0081024 A1* | 4/2008 | Beasley et al. | 424/59 |
| 2009/0285768 A1* | 11/2009 | Baker et al. | 424/59 |
| 2010/0135916 A1* | 6/2010 | Courel et al. | 424/47 |
| 2010/0247800 A1* | 9/2010 | Willey et al. | 427/553 |

FOREIGN PATENT DOCUMENTS

| | | |
|---|---|---|
| GB | 1334636 | 10/1973 |
| JP | 53-078985 | 7/1978 |
| JP | 55-045527 | 11/1980 |
| JP | 11-193224 | 7/1999 |
| JP | 2003/335644 | 11/2003 |
| WO | 01/06829 A2 | 2/2001 |
| WO | 2007/127065 | 11/2007 |

OTHER PUBLICATIONS

All Office Actions, U.S. Appl. No. 12/433,958.
ISR dated Jan. 24, 2011, PCT/US2010/056287, 4 pages.
ISR dated Dec. 8, 2009, PCT/US2009/042324, 7 pages.

* cited by examiner

*Primary Examiner* — Charles Boyer
(74) *Attorney, Agent, or Firm* — Angela K. Haughey

(57) ABSTRACT

The present invention relates to a composition including an active material having groups capable of covalent attachment to a substrate in the presence of an acid or a base, a photocatalyst capable of generating an acid or a base upon exposure to light, and a vehicle. The active is a silicone polymer and/or a silicone oligomer, having a molecular weight higher than 1,000 grams/mole, and at least one organic functional group. The compositions may also include surfactants, emulsifiers, oxidants, and other components. A method for treating a substrate is also disclosed. The compositions and methods described herein are useful in personal care product and consumer care product applications.

21 Claims, 5 Drawing Sheets

COMPOSITIONS AND METHODS INCORPORATING PHOTOCATALYSTS

CROSS REFERENCE TO RELATED APPLICATION

This application claims the benefit of U.S. Provisional Application Ser. No. 61/260,900 filed Nov. 13, 2009.

FIELD OF THE INVENTION

A composition for and method of covalent modification of surface properties of a substrate, comprising an silicone polymer and/or oligomer active material having functional groups capable of covalent attachment to a substrate in the presence of an acid or a base, a photocatalyst capable of generating an acid or a base upon exposure to light, and a vehicle.

BACKGROUND OF THE INVENTION

Materials may be characterized in terms of bulk properties and surface properties. The overall properties of a material are controlled in significant part by the surface properties and the bulk properties of the material. The surface properties of a material are largely controlled by the surface chemistry and surface structure of the material. The bulk properties of a material are largely controlled by the bulk chemistry and bulk structure of the material. It is sometimes desirable to modify the surface chemistry and/or surface structure of a material in order to produce certain surface properties. In addition, it is sometimes desirable to modify the bulk chemistry and/or bulk structure of a material in order to produce certain bulk properties.

Hair and skin are physiological materials of particular interest in terms of surface and/or bulk modification. Hair and skin are exposed to a variety of chemical and physical environments. For example, common hair care practices often include one or more of washing, blow drying, brushing, coloring, perming, relaxing, styling, and the like. These activities repeatedly expose hair to mechanical and chemical factors that may result in the loss of the natural luster and texture that characterizes healthy hair. Moreover, environmental factors may add to these effects and substantially contribute to weathered or damaged hair. Skin also suffers from surface damage as a result of similar mechanical, chemical and environmental factors. Acute damage to the surface of hair and skin may build over time, resulting in chronic damage.

Hair is naturally protected from mechanical, chemical, and environmental mediated damage by the fiber cuticle surface membrane ("FCSM"). The FCSM comprises the outermost surface layer of hair fibers and includes protein and lipid components. The FCSM functions as a highly resistant, hydrophobic, surface-protective barrier to mechanical, chemical and environmental factors that would otherwise substantially contribute to hair damage. The FCSM comprises a surface lipid mono-layer, sometimes referred to as the F-layer, covalently bound to an underlying layer of heavily cross-linked keratinous protein, sometimes referred to as the epicuticle. The F-layer comprises predominately fatty acids such as 18-methyl-eicosanoic acid ("18-MEA") bound to the epicuticle through thioester linkages formed between the thiol groups on the cysteine residues in the keratin and other proteins in the epicuticle and the carboxyl group on the 18-MEA or other fatty acid. The F-layer gives hair fibers a hydrophobic surface, which in part facilitates the shiny luster, silky texture and smoothness of healthy hair.

Skin is naturally protected from mechanical, chemical, and environmental mediated damage by the stratum corneum. The stratum corneum is the outermost layer of epidermis. The stratum corneum comprises lipid-depleted keratinous cells embedded in a lipid-rich interstitium comprising keratin, fatty acids and ceramides. The fatty acids, ceramides and other lipid components of the stratum corneum are thought to be covalently attached to the proteinaceous components through ester and thioester linkages in a manner similar to the covalent attachment of the F-layer to the epicuticle in hair. The stratum corneum functions to prevent percutaneous moisture loss, regulate percutaneous absorption, and provide a physiologic barrier to protect the lower layers of the epidermis.

Despite differences in microstructure, the F-layer and the stratum corneum both possess similar protective functions for hair and skin respectively. However, mechanical, chemical and environmental factors may result in loss of at least a portion of the F-layer and the stratum corneum. For example, during permanent hair coloring, the combinations of hydrogen peroxide, ammonia and high pH may remove at least a portion of the protective F-layer, allowing for additional oxidation of the underlying hair surface, which may cause irreversible physiochemical changes in the hair fibers. Repeated colorings may cause the F-layer to completely disappear from the surface of hair fibers. As a result, the previously hydrophobic hair fiber surfaces may become hydrophilic because the keratinous epicuticle is exposed to the surface when the F-layer is lost. The natural protective and lubricating properties of the hair fiber surface are consequently diminished, and hair may feel dry, rough, frizzy, become difficult to brush and/or detangle, appear duller and less colorful, possess increased levels of static, and become substantially more susceptible to additional damage due to other mechanical, chemical and environmental factors.

The stratum corneum is similarly susceptible to damage mediated by mechanical, chemical and environmental factors. For example, during the winter months in relatively cold climates, lower humidity levels, low temperatures, and high winds may contribute to xerosis (dry skin), characterized, for example, by redness, itchiness and/or flaking. Damaged skin is substantially more susceptible to further damage, which may transform an acute problem to a chronic condition.

Damage to the surface portions of these materials may lead to damage to the underlying bulk portions of the materials. This may ultimately result in substantial, and perhaps irreparable, damage to these materials. A variety of mechanical, chemical and environmental factors may contribute (solely or collectively) to hair and/or skin damage. For example, excessive exposure to sunlight, exposure to chlorine in pool water (and to a lesser extent in the water provided by municipal supply), exposure to other forms of water pollution, exposure to various forms of air pollution, frictional interactions between hair fibers, and frictional interaction between hair fibers or skin and other surfaces may contribute to hair and skin damage.

Accordingly, there exists a need for compositions and methods to compensate for F-layer and stratum corneum loss from hair fibers and skin, respectively, that provides a durable conditioning and protective benefit. Covalent modification of the surface properties of damaged hair and skin is one example of such an approach. There is also a need to protect, repair, and/or strengthen these materials. Modification of the surface of a material by locally forming an active material on the material surface by reacting one or more active components to create covalent bonds between the one or more active components and modification the bulk of a material by forming active material in a similar manner within the bulk of the material are promising approaches.

SUMMARY OF THE INVENTION

A personal care composition comprising: an active material having one or more functional groups capable of covalent attachment in the presence of an acid or a base to one or more complementary functional groups; a photocatalyst capable of generating an acid or a base upon exposure to light; and a physiological acceptable vehicle for dispersing or dissolving the active material and the photocatalyst for application of the composition to a substrate; and
wherein the vehicle is a physiological acceptable vehicle and the substrate is selected from the group consisting of hair, skin, nail, teeth and combinations thereof;
wherein the active material is selected from the group consisting of a silicone polymer and a silicone oligomer, and wherein the active has molecular weight higher than 1000 grams/mole, and at least one organic functional group.

A method for treating a substrate comprising: applying at least one active material to the substrate, the active material having one or more functional groups, and the substrate having one or more complementary functional groups; applying to the substrate at least one photocatalyst capable of generating an acid or base on exposure to light; and exposing the photocatalyst and the at least one active material to light for forming covalent attachments between the one or more functional groups of the at least one active material and a reagent selected from the group consisting of a second active material, a substrate and a combination thereof; wherein the active material is selected from the group consisting of a silicone polymer and a silicone oligomer, and wherein the active has molecular weight higher than 1000 grams/mole, and at least one organic functional group.

BRIEF DESCRIPTION OF THE DRAWINGS

Various embodiments described herein may be understood by reference to the following description, taken with the accompanying drawings as follows.

DETAILED DESCRIPTION OF THE INVENTION

Figure 1:
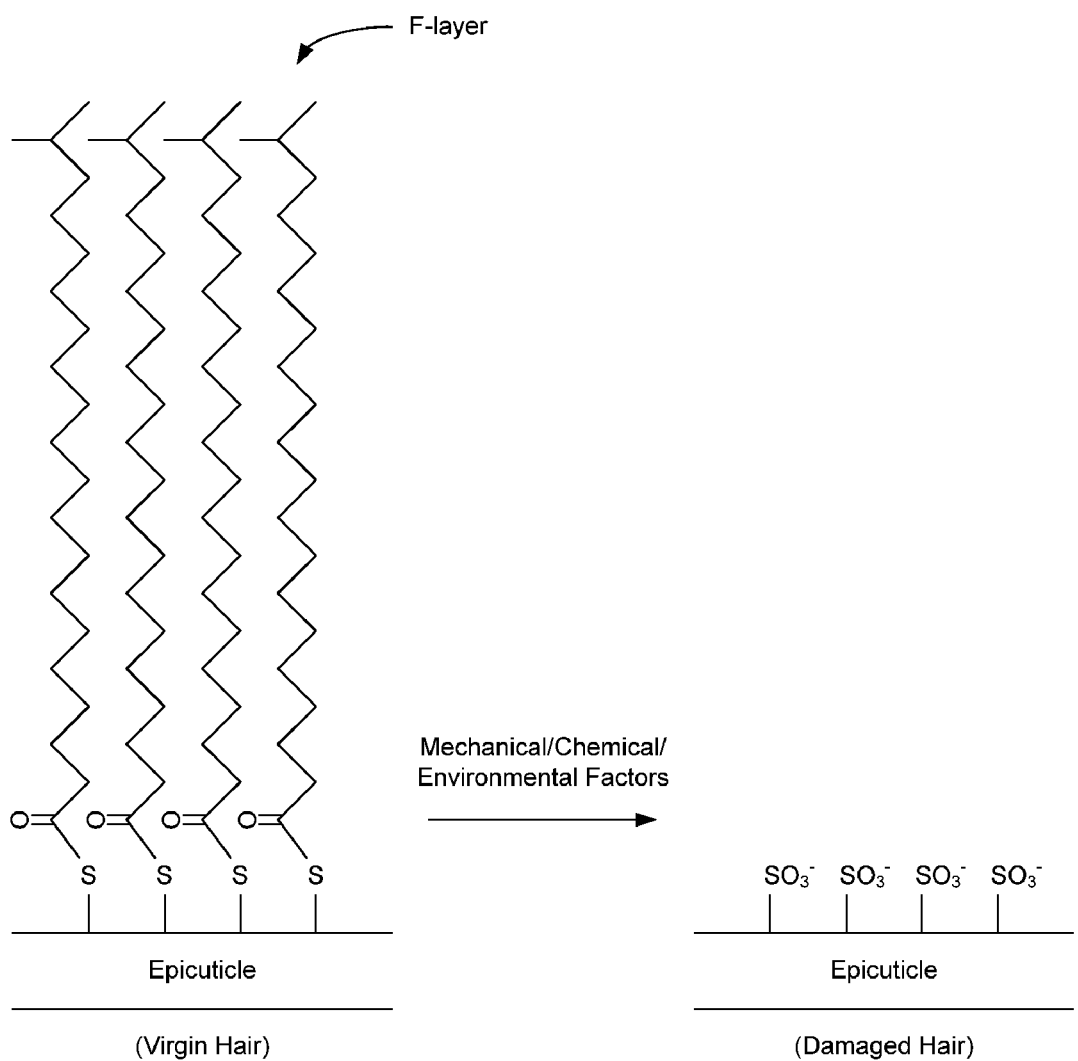
FIG. 1 is a schematic diagram that illustrates damage to the FCSM of a hair fiber comprising a keratinous epicuticle portion covalently bound to 18-MEA by way of thioester bonds.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

As used herein, the term "functional group" means an atom or group of associated atoms that, at least in part, defines the structure and determines the properties of a particular family of chemical compounds. A functional group may be a region on or in a molecule or material that is a site of specific chemical reactivity compared to other regions of the molecule or material. Functional groups generally have characteristic properties and may control, in part, the reactivity of a molecule as a whole. Functional groups include, but are not limited to, hydroxyl groups, thiol groups, carbonyl groups, carboxyl groups, sulfonate groups, sulfide groups, ether groups, halogen atoms, amino groups, cyano groups, nitro groups, and the like. Compounds that are generally classified (structurally and/or functionally) according to functional groups include, but are not limited to, alkanes, alkenes, alkynes, aromatic compounds, halides, alcohols, ethers, esters, amines, imines, imides, carboxylic acids, amides, acid halides, acid anhydrides, nitriles, ketones, aldehydes, carbonates, peroxides, hydroperoxides, carbohydrates, acetals, epoxides, sulfonic acids, sulfonate esters, sulfides, sulfoxides, thioethers, thiocyanates, disulfides, phosphonic acids, phosphate esters, phosphines, azides, azo compounds, nitro compounds, nitrates, nitriles, nitrites, nitroso compounds, thiols, cyanates, and isocyanates, for example.

The terms "active material", "active component", "active compound", and combinations and modifications of these terms, as used herein means substances to be applied to a substrate to modify the surface and/or bulk properties of the substrate material. These terms may be used interchangeably. Substrate surface properties may include, for example, surface hydrophobicity/hydrophilicity, oleophobicity/oleophilicity, color, optical properties, absorptivity, adsorptivity, bonding capability, brightness, dullness, frictional resistance, stain resistance, surface texture, odor, washability, wettability, elasticity, plasticity, and rigidity. Substrate bulk properties may include, for example, tensile strength, rigidity, absorptivity, elasticity, plasticity, and biological activity.

Active materials may include compounds having one or more functional groups capable of covalent attachment in the presence of an acid or a base to one or more complementary functional groups present at the surface or in the bulk of a substrate. Active materials may also include compounds capable of forming covalent bonds between molecules in the presence of an acid or a base, for example, monomers capable of acid or base catalyzed polymerization. A "cosmetically active material" is an active material suitable for use in a personal care product without undue toxicity, incompatibility, instability, allergic response, and the like.

The term "monomer" as used herein means a compound that may be covalently bonded to other monomers (that may have the same or different chemical structures) to form a polymer or copolymer. The term "polymer" (and "copolymer") as used herein means a compound comprising a plurality of monomers. Accordingly, as used herein the term polymer includes dimers, trimers, oligomers, and the like.

As used herein, the terms "modify", "modification", "functionalize" or "functionalization", with regard to a substrate, refers to (1) covalently attaching an active component to the substrate surface, (2) covalently attaching an active component to the substrate in the bulk of the substrate material, (3) forming covalent bonds between two or more active components (which may be the same or different chemical moieties) where the resultant secondary active material localizes to the substrate surface, and/or (4) forming covalent bonds between two or more actives (which may be the same or different chemical moieties) where the actives are present within the bulk of the substrate.

The term "suitable for application to human hair" and "suitable for application to human skin" as used herein means that the compositions or components thereof so described are suitable for use in contact with human hair and the scalp and skin without undue toxicity, incompatibility, instability, allergic response, and the like.

The term "shampoo" as used herein means a composition for cleaning hair or skin, including scalp, face, and body. Accordingly, the term "shampoo" includes, but is not limited to, the conventional understanding of a hair shampoo, a body wash, a face wash, or other surface washing composition, for example. In addition, the term "shampoo" includes compositions for use on humans and/or animals.

The term "conditioner" as used herein means a composition for treating hair or skin, including scalp, face, and body, in order to provide protection to hair or skin from mechanical, chemical, and/or environmental factors that contribute to damaged or weathered hair or skin, and/or to alleviate the characteristics of such damage. Accordingly, the term "conditioner" includes, but is not limited to, the conventional understanding of a hair conditioner (leave-in and/or rinse-out), a skin lotion, or a facial moisturizer, for example. In addition, the term "conditioner" includes compositions for use on humans and/or animals.

The term "personal care product" as used herein means a product such as, for example, lipstick, mascara, rouge, foundation, blush, eyeliner, lipliner, lip gloss, other cosmetics, facial powder, body powder, sunscreen, sun block, nail polish, mousse, hair spray, styling gel, nail conditioner, bath gel, shower gel, body wash, face wash, shampoo, hair conditioner (leave-in or rinse-out), cream rinse, hair dye, hair coloring product, hair shine product, hair serum, hair anti-frizz product, hair split-end repair product, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, after shaving product, cleanser, skin gel, rinse, toothpaste, mouthwash, or oral care strips.

The term "consumer care product" as used herein means a product such as, for example, soft surface cleaner, a hard surface cleaner, a glass cleaner, a ceramic tile cleaner, a toilet bowl cleaner, a wood cleaner, a multi-surface cleaner, a surface disinfectant, a dishwashing composition, a laundry detergent, a fabric conditioner, a fabric dye, a surface protectant, a surface disinfectant, motor vehicle surface treatment, and the like. Consumer care products may be in the form of liquids, gels, suspensions, powders, and the like. Consumer care products may also be for household or home care use as well as for professional, commercial and/or industrial use.

One object of the compositions and methods described herein is to provide for the modification of the surface and/or bulk properties of a substrate by covalently attaching an active material to the surface of the substrate. Another object of the compositions and methods described herein to provide for the modification of the surface and/or bulk properties of a substrate by treating the substrate with an active compound capable of reacting with itself to form covalent bonds between two or more molecules of the active compound thereby forming a secondary active material. It is still another object of the compositions and methods described herein to provide for the functionalization of the surface of a substrate by covalently attaching active material to the surface of the substrate. In order to achieve effective treatment, it is occasionally desirable to initially attach onto a substrate a material that contains multiple similar functional groups in its molecule, followed by another step of attaching another material/benefit agent by reacting with the initially attached material. This is especially useful if the substrate contains only limited density of functional groups that are able to react with a benefit agent towards a chemical bond. For Example, initial attachment of malic acid (2-hydroxy-1,4-dibutanoic acid) onto a substrate increases the reactivity of the substrate by a factor of two towards subsequent attachment of an active. It is yet another object of the compositions and methods described herein to provide for such modification/functionalization in a manner that is readily amenable to health and safety regulations, and which may be readily implemented in a personal care product and/or a consumer care product space.

The various embodiments relate, in general, to compositions and methods for treating a substrate. As used herein, the term "substrate" means any material for which it is useful to treat the surface and/or bulk with the compositions and methods described herein, including, but not limited to, physiological materials such as, for example, hair fibers, skin, nails, gums, and teeth. Substrate may also mean non-physiological materials such as, for example, fabric, paper, wood, plastic, glass, tile, stone, concrete, brick, other ceramics, coated or painted metal surfaces, coated glass, polymeric films, and composites. Substrates may also include surfaces that have been previously modified such as, for example, coated surfaces (e.g., varnished or painted) or laminated surfaces. The terms "substrate" and "material" may be used interchangeably in the context of substances to be modified by the compositions and methods described herein.

In various embodiments, the compositions described herein include an active component that can modify a substrate in the presence of an acid or a base, a photocatalyst capable of generating an acid or a base upon exposure to light, and a suitable vehicle, which may optionally be a physiological acceptable vehicle. In various embodiments, the compositions described herein may also include one or more optional components, including surfactants, emulsifiers, oxidants, reductants, pH regulators, emollients, humectants, proteins, peptides, amino acids, additive polymers, glossers, essential oils and/or fatty acids, lubricants, sequestrants/chelators, antistatic agents, rheology modifiers, feel agents, fillers, preservatives, perfumes, other functional components, or combinations thereof.

In various embodiments, the methods described herein include treating a substrate by forming one or more covalent bonds between an active component and/or the substrate, where the covalent bond is formed in the presence of an acid or base generated by a photocatalyst upon exposure to light. In various embodiments, the methods described herein include treating a substrate by forming one or more covalent bonds between two or more active component molecules, where the covalent bond is formed in the presence of an acid or base generated by a photocatalyst upon exposure to light and the active material localizes to the surface and/or bulk of the substrate. As used herein, the term "molecule" means a sufficiently stable group of at least two atoms in a definite arrangement held together by chemical bonds. Accordingly, the term molecule includes, but is not limited to, neutral molecular compounds, polyatomic ions, radical species, biomolecules, monomers, dimers, trimers, oligomers, polymers, and the like.

In various embodiments, the methods described herein include treating a substrate by preparing and covalently bonding a compound to the substrate, or forming covalent bonds between compounds on the substrate surface or in the substrate bulk, in situ, by providing a substrate, providing one or more reagents, providing a photocatalyst, and exposing the photocatalyst to light in the presence of the substrate and the one or more reagents, where the photocatalyst generates an acid or a base, the acid or the base catalyzes reaction between the one or more reagents and/or reaction between the one or more reagents and the substrate, and where the reaction(s) forms covalent bonds. In various embodiments, the methods described herein include providing a system including a substrate, an active component that can modify a substrate in the presence of an acid or a base, and a photocatalyst capable of generating an acid or a base upon exposure to light, and exposing the system to light.

Generally, covalent attachment of active components on substrates such as hair and skin, for example, often proves difficult to achieve. This is especially true in the presence of water, which may rapidly degrade reactive moieties before substrate functionalization occurs. Moreover, aqueous media are known to chemically facilitate hydrolysis and oxidation reactions that may compete against covalent attachment of active components to substrates. This may pose particular problems, for example, in personal care products where water is often used as a physiologically acceptable vehicle. Consumer care products also often use water in a variety of capacities, most notably as a solvent.

In addition, substrates such as, for example, hair, skin, fabric, glass and ceramic may not contain particularly reactive chemical functional groups on the surface that would readily react with active components to form covalent bonds. This relatively low substrate surface reactivity may result in a reaction system that is outside the practical time frame of an apply-and-rinse environment (e.g., shampooing and conditioning hair, washing skin, laundering fabrics, or cleaning hard surfaces). Furthermore, strict regulatory requirements concerning product safety and environmental protection increase the challenge of providing compositions and methods for treating a substrate such as, for example, hair, skin, fabric, glass or ceramic, through covalent attachment of active components.

However, the various embodiments of the compositions and methods described herein are directed toward a photocatalyst technology that allows the use of light to promote a reaction such as, for example, the covalent attachment of an active component to a substrate or formation of covalent bonds between two or more active components in situ on the surface or in the bulk of a substrate material. The various embodiments may be used, for example, to promote the covalent attachment of long-chain alkyl groups to damaged hydrophilic hair and/or skin in order to replenish and/or fortify the normally hydrophobic character of these substrates. In addition, the various embodiments may be used, for example, to promote the covalent attachment of active materials to fabrics or hard surfaces. Furthermore, the various embodiments may be used, for example, to locally polymerize monomers on the surface and/or in the bulk of substrate materials in order to modify the surface and/or bulk properties of a material.

In various embodiments, covalent attachment may yield a variety of substantial benefits to individuals that possess damaged hair and/or skin. For example, hair conditioning benefits may include, among others, improved feel, lower friction, easier combing/brushing, reduced dryness, increased smoothness, decreased frizziness, increased shine, decreased levels of static, and improved protection against damage due to other mechanical, chemical and environmental factors. Skin conditioning benefits may include, among others, decreased dryness, decreased redness, decreased itchiness, decreased flaking, and improved texture and smoothness. At least some of these benefits may be imparted by increased or targeted deposition of actives resulting from the surface modification via covalent attachment. The benefits imparted by the compositions and methods described herein are potentially more durable because a non-labile covalent bond is employed, which is generally stronger and more stable relative to the absorption, adsorption, hydrogen bonding, ionic bonding, other electrostatic interactions, and/or other transient non-covalent associations employed in prior conditioners to deposit or apply active components onto hair and/or skin. This may substantially reduce the frequency of application and reapplication encountered with prior conditioners.

Various embodiments of the compositions and methods described herein provide for the covalent attachment of active components to substrates, which may be described as an approach toward repairing and/or fortifying the hair F-layer or skin stratum corneum for example. In the context of hair, and not to be bound or otherwise limited by theory, the F-layer of virgin hair may be stripped from the hair fiber by processes mediated by various mechanical, chemical, and/or environmental factors as illustrated in FIG. 1. These processes may include, for example, the oxidative and hydrolytic reactions commonly encountered during permanent hair coloring and permanent waving processes.

FIG. 1 is a schematic diagram that illustrates the FCSM of a hair fiber comprising a keratinous epicuticle portion covalently bound to 18-MEA by way of thioester bonds between the carboxyl group on the 18-MEA and the thiol group on cysteine residues in the keratin protein in the epicuticle. Hydrolytic and/or oxidative processes (for example, due to the combinations of hydrogen peroxide, ammonia and high pH commonly encountered during permanent hair coloring and permanent waving processes), as well as other mechanical, chemical, and environmental factors, may remove at least a portion of the F-layer by cleaving the cysteine-lipid thioester bond, leaving exposed epicuticle comprising sulfonate groups on the cysteine residues.

The anionic sulfonate groups on the cysteine residues at the surface of the epicuticle render the surface of any damaged hair fibers hydrophilic, which may result in the undesirable properties of damaged hair. Moreover, it has been observed that the more hydrophilic (and consequently the more damaged) the hair fibers, the lower the deposition of prior hydrophobic conditioning actives (such as, for example, dimethylsiloxanes, fatty alcohols and acids, and quaternary amines) by non-covalent interactions and associations. Accordingly, the compositions and methods described herein provide an attractive approach for treating such damaged substrates.

Figure 2:
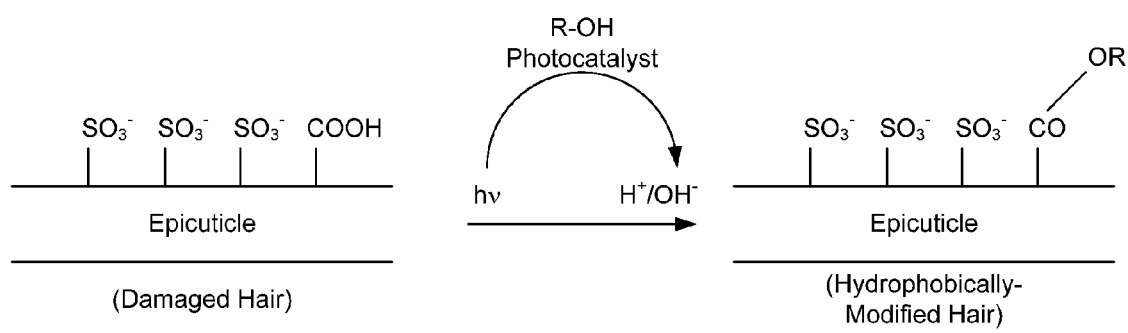
FIG. 2 is a schematic diagram that illustrates one non-limiting embodiment of the compositions and methods described herein for treating physiological substrates such as hair with an active component and a photocatalyst.

FIG. 2 schematically illustrates one non-limiting embodiment of the compositions and methods described herein for treating substrates. A composition comprising an active component having a hydroxyl group (R—OH) and a photocatalyst capable of generating an acid or a base upon exposure to light is provided in the presence of a substrate comprising surface sulfonate and carboxyl groups. The photocatalyst is exposed to light, which causes the photocatalyst to form an acid or a base. The acid or base catalyzes the formation of a covalent ester bond between the hydroxyl group on the active material and the carboxyl group on the substrate.

Figure 3:
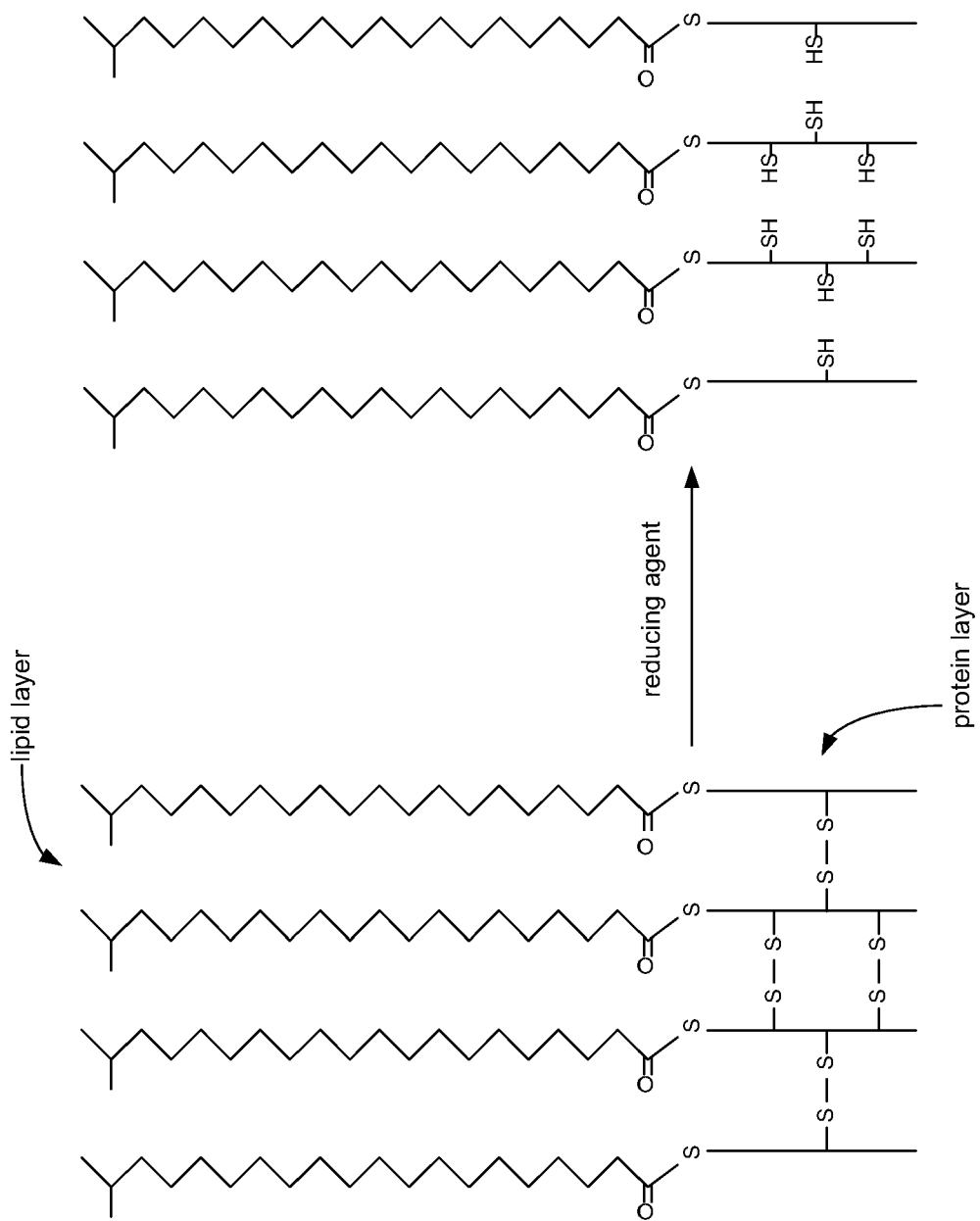
FIGS. 3 and 3A are schematic diagrams that illustrate one non-limiting embodiment of the compositions and methods described herein for treating physiological substrates such as hair with an active component and a photocatalyst.
Figure 3A:
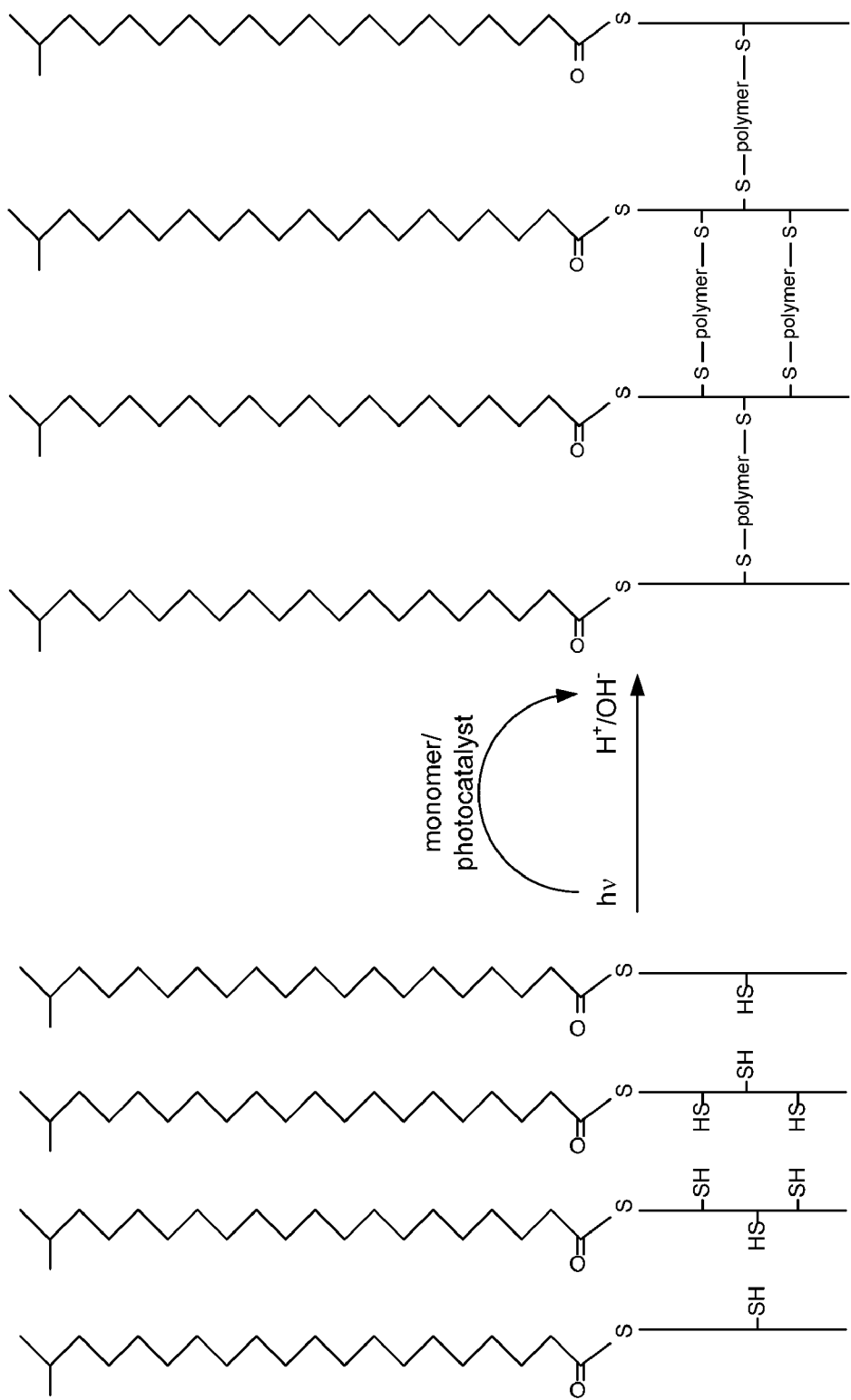

FIG. 3 and FIG. 3A, viewed together, schematically illustrate one non-limiting embodiment of the compositions and methods described herein for treating substrates. A portion of a hair fiber comprising a lipid layer (F-layer) and a protein layer (epicuticle) is shown. The protein layer comprises structural proteins such as, for example, keratin having disulfide bonds between cysteine residues. The hair may be treated with a reducing agent to break the disulfide bonds and form respective thiol groups. The hair may be further treated with an active component comprising one or more compounds capable of reaction to form covalent bonds between the one or more active component compounds and/or between the one or more active component compounds and the thiol groups. The hair fiber is also treated with a photocatalyst. The one or more active components and the photocatalyst penetrate the surface of the hair fiber substrate. The hair fiber substrate treated with the one or more active components and photocatalyst is exposed to light of suitable wavelength to activate the photocatalyst and catalyze reaction between the one or more active components within the hair fiber substrate and the thiol groups.

In various embodiments, the active components may be one or more monomers capable of polymerizing in the presence of acid or base. The hair fibers are treated with a composition comprising photocatalyst and monomer, which at least partially penetrates the fiber. Upon exposure to light, the photocatalyst is activated thereby generating acid or base, which catalyzes the polymerization of the monomer, thereby forming a polymer in situ, which may optionally attach to the hair fiber by way of covalent bonds formed between the thiol groups and the polymer.

In other embodiments (not shown), the polymer does not covalently attach to the hair fiber. For example, the polymer formed in situ may be physically immobilized on the surface of the hair fiber or within pores in the hair fiber. The polymer formed in situ may also be associated with the hair fiber by a physical and/or chemical interaction such as, for example, adsorption, absorption, electrostatic interaction, frictional interaction, steric interaction, and/or size exclusion effects with the surface and/or bulk of the substrate.

In various embodiments, the monomer may be styrene or a styrene derivative such as, for example, α-methyl styrene. The monomer may also comprise mixtures of different monomers such that the in situ polymerization (on the surface and/or in the bulk of the substrate) produces copolymer.

In various embodiments of the compositions and methods described herein, the photocatalyst may be a photoacid that deprotonates upon exposure to light. The proton (which may be solvated, e.g., in the form of a hydronium ion) may catalyze the formation of a covalent bond through an esterification reaction or a thioesterification reaction, for example. In various embodiments of the compositions and methods described herein, the photocatalyst may be a photobase that generates hydroxide anion upon exposure to light. The hydroxide anion may catalyze the formation of a covalent bond through an esterification reaction or thioesterification reaction, for example. In various embodiments, the mechanism of action of a photoacid or photobase is not limited to an Arrhenius-type or Brønsted-Lowry type acid or base system, but rather may also include a Lewis-type acid or base that is catalytically activated upon exposure to light. The compositions and methods described herein are not limited in this context.

Esterification reactions are generally reversible. In relatively neutral media, such as water, the reversible esterification reaction may not thermodynamically favor the formation of the ester bond and water, as opposed to the reverse reaction of hydrolysis of the ester bond to respective hydroxyl and carboxyl containing moieties. Thioesterification systems generally behave in an analogous manner. Thus, the formation of covalent bonds between active components and substrates in prior systems, for example in prior conditioners, was impracticable in the context of treating substrates such as, for example, hair or skin.

In addition, acid or base catalysis of esterification or thioesterification reactions are generally impracticable in the context of personal care products because it is difficult to generate sufficient acid or base concentration at the surface or within the bulk of the substrate without having relatively high or relatively low pH. The use of products having relatively high or relatively low pH is generally inappropriate because such acidic and caustic substances may be physiologically unacceptable.

The compositions and methods described herein overcome these limitations. The use of a photocatalyst allows for the co-localization of the catalyst and an active component at a substrate surface or within the bulk of the substrate material. The photocatalyst however is not activated until it is exposed to light. Photoacid catalysts, for example, exhibit a decrease in pKa upon exposure to light of suitable wavelength. Photobase catalysts, for example, may exhibit an increase in pKb upon exposure to light of a suitable wavelength. The respective increase in acid or base strength upon exposure to light results in a localized increase in proton or hydroxide concentration at the substrate surface which facilitates rapid esterification or thioesterification, for example. Moreover, because the proton or hydroxide concentration is localized at the substrate surface for a short period of time (before diffusing into the surrounding medium), bulk pH may be essentially unaffected by the photocatalytic reaction and may remain close to neutral, given the quantity of the photocatalyst used. This is advantageous for physiological applications such as, for example, in personal care products and in various consumer care product applications. In addition, the transient localized nature of the acidic or basic catalysis also contributes to the stability of the covalent bond formed during the process in cases where the covalent bond is sensitive to high or low pH.

Therefore, photocatalysis of the reactions forming ester and/or thioester covalent bonds between active components and substrates in the various embodiments of the compositions and methods described herein provides for an efficient, controllable, stable and physiologically acceptable approach to substrate treatment such as, for example, F-layer and stratum corneum repair and/or fortification in hair and skin respectively.

Figure 4:
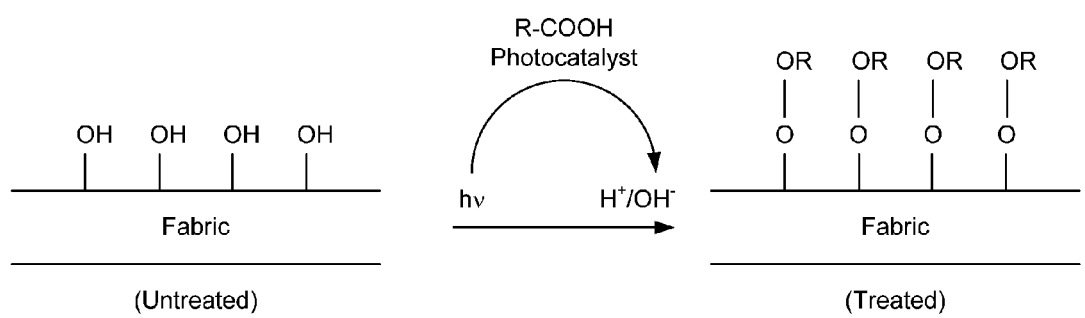
FIG. 4 is a schematic representation of one non-limiting embodiment of a mechanism of action of the compositions and methods described herein where a substrate surface is covalently modified.

FIG. 4 is a schematic representation of one non-limiting embodiment of a mechanism of use of the compositions and methods described herein in the context of a photoacid catalyst. In the first step, a reagent solution is provided that includes a reagent, which may be an active component, and a photoacid catalyst. The reagent solution may comprise a shampoo, a conditioner, other personal care product or a consumer care product. In the second step, the reagent solution is applied to a substrate, which may be skin, hair, fabric, or a hard surface, for example. The components of the reagent solution deposit on the surface of the substrate. In the third step, the system comprising the reagent solution and the substrate is exposed to light. The light causes the deprotonation of the photocatalyst. In the fourth step, a photoacid-catalyzed esterification reaction occurs between the reagent and the substrate surface. In the fifth step, un-reacted catalyst, reagent, and protons diffuse from the substrate surface and are removed from the system. In the sixth step, the modified/functionalized substrate is dried. In the seventh step, the modified/functionalized substrate is washed and rinsed. The modified/functionalized substrate substantially retains the covalently bound reagent after washing and rinsing.

The compositions and methods described herein facilitate in situ and localized modification of material properties in a controlled manner. The active components are covalently altered (e.g., by the formation of covalent bonds between active components to form a secondary active material and/or between active components and a substrate material) in a photoacid or photobase reaction system.

The substrate to be modified may be treated by spraying, soaking, spreading, coating, rinsing, or any other suitable means of introducing the composition onto the surface of the substrate or into the bulk of the substrate material. In various embodiments, it is important to ensure the entire surface of the substrate is wetted by reagent solution in order to ensure sufficient modification of the substrate surface and/or bulk. If the active material is at least partially insoluble in the vehicle, it is important to maximize contact between the active and the substrate by, for example, minimizing the drop size or particle size of the active in the vehicle. In various embodiments, it may be desired to introduce reagent solution onto only a single portion or multiple portions of a substrate surface. In other embodiments, it may be desired to irradiate only a single portion or multiple portions of a substrate surface with light of a wavelength suitable to activate the photocatalyst. The covalent modification only occurs on those areas of the substrate surface (and underlying bulk) that are both in contact with a reagent solution and irradiated with light of a wavelength suitable to activate the photocatalyst. This allows for control of the location and extent of the surface and/or bulk modification.

The acid or base photocatalytic covalent modification/functionalization mechanisms described herein may also be reversible. For example, substrate surfaces covalently modified or functionalized through esterification and/or thioesterification reactions may be contacted with an acidic aqueous surfactant solution. Alternatively, an alkaline surfactant solution may be employed. These solutions may facilitate the hydrolytic cleavage of the ester and/or thioester bonds attaching the active components to the substrate, thereby removing the active components.

This removability is limited to active component-substrate bonds that are reversible under the appropriate conditions. For example, in the case of photoacid-catalyzed esterification, the ester bond is formed when the reagent and the catalyst are present in the vicinity of the substrate and exposed to the appropriate light. The high concentration of protons at the moment of irradiation results in ester bond formation that remains intact because the generated protons diffuse rapidly into the bulk of the medium. The low content of the photoacid allows for subsequent stable and near-neutral pH of the bulk aqueous solution. Under these conditions the ester bond is hydrolyzed at a very slow rate. However, treatment with significantly lower (or significantly higher) pH aqueous solutions will more readily break the ester bonds resulting in the original unmodified substrate surface.

The removal of the covalently-attached active can also be achieved by treatment of the modified or functionalized substrate with a composition including a photocatalyst (photoacid or photobase). This allows for improved control over the timing of the removal of the active component from the substrate. This can be achieved if the photocatalyst is chosen so that it is unaffected by ambient light but can generate acid or base species under light of a specific wavelength provided by an appropriate device.

Each of the various components of the compositions and associated methods described herein, as well as preferred and optional components, are described in detail.

Active Component

The active of the present invention includes a silicone oligomer or polymer having i) a molecular weight higher than 1000 grams/mole in one embodiment, and in another embodiment a molecular weight higher than 50,000 grams/mole, ii) at least one organic functional group (and in one embodiment multiple groups), including but not limited to hydroxyl, amino, carboxyl groups and/or any combination thereof, and iii) the level and nature of substitution and molecular weight of the silicone polymer can be appropriately selected, depending on the desired substrate modification and application conditions. For example, if increased hydrophobicity is desired, less than 2% of the silicone atoms of the silicone oligomer or polymer can be substituted with organic groups. The silicone copolymer can be from monomers which contain organic alcohol groups (primary and secondary) including those having the structure:

Wherein R1, R2 methyl; R3-CH2CH2CH2-(OCH2CH2O)q-H with q≧1.

Hair modification can be achieved by treating damaged hair with a silicone oligomer or polymer active. Treatment with such active in emulsion, dispersion, and/or solutions with a photoacid generator, such as 8-hydroxyquinoline can provide damaged hair with benefits that are durable, for example, that are persistent after multiple shampoo wash cycles. Examples of durable benefits include hair softness (wet and dry), combability, anti-frizz, style and color retention, moisturization, and shine.

The surface modification method involves formation of covalent bonds between silicone polymer and the substrate. The bonds are created by acid-catalyzed reaction of the primary or secondary alcohol of the oligomer or polymer with compatible functional groups of the hair substrate (for example carboxylic acid groups toward condensation).

Suitable silicone oligomers and/or polymers include a silicone oligomer or polymer having an alkoxyalkanol group. In one embodiment the silicone oligomer and/or polymer is a Bis-Hydroxyethoxypropyl Dimethicone having the structure:

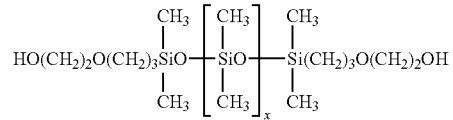

Suitable Bis-Hydroxyethoxypropyl Dimethicones include, but are not limited to, those materials available as 5562 Carbinol Fluid from Dow Corning, and Baysilone OF OH 702 E from Momentive.

Photocatalyst

The photocatalyst may be any acid, base (or conjugate thereof) having a pKa (or pKb) value that decreases (or increases) upon exposure to light. The light may be light of any suitable wavelength to result in the respective decrease or increase in pKa or pKb. For example the light may be ambient light, sunlight, incandescent light, fluorescent light, LED light, laser light, and the like. The light may fall within any classification along the electromagnetic spectrum, such as, for example, visible light, near or far ultraviolet light, or near or far infrared light. It will be readily apparent to one of ordinary skill in the art that the appropriate wavelength or wavelengths of light will be dependant upon the identities of the one or more photocatalysts employed.

In addition, the suitable light may be provided from any source capable of illuminating the substrate surface. For example, ambient sunlight, incandescent light, fluorescent light, and the like may provide light of suitable wavelength. Accordingly, the light may be provided by conventional sources such as lamps and portable or battery-powered lights. In addition, specific devices may be developed or adapted for use with the compositions and method described herein. For example, a hair brush configured to incorporate LEDs that provide light of a suitable wavelength may be used to covalently modify the surface of hair fibers. In various embodiments, a laser may be used to provide precise targeting of the covalent modification of substrate surfaces, for example.

In various embodiments, the photocatalyst is a photoacid such as, for example, an aromatic hydroxy compound, a sulfonated pyrene compound, an onium salt, a diazomethane derivative, a bissulfone derivative, a disulfuno derivative, a nitrobenzyl sulfonate derivate, a sulfonic acid ester derivative, a sulfonic acid ester of an N-hydroxyimide, or combinations thereof.

Photoacid catalysts may include, for example, hydroxy-substituted aromatics such as, for example, 8-hydroxyquinoline, 8-hydroxyquinoline sulfate, 8-quinolinol-1-oxide, 5-hydroxyquinoline, 6-hydroxyquinoline, 7-hydroxyquinoline, 5-iodo-7-sulfo-8-hydroxyquinoline, 5-fluoro-8-hydroxyquinoline, 5-fluoro-7-chloro-8-hydroxyquinoline, 5-fluoro-7-bromo-8-hydroxyquinoline, 5-fluoro-7-iodo-8-hydroxyquinoline, 7-fluoro-8-hydroxyquinoline, 5-chloro-8-hydroxyquinoline, 5,7-dichloro-8-hydroxyquinoline, 5-chloro-7-bromo-8-hydroxyquinoline, 5-chloro-7-iodo-8-hydroxyquinoline, 7-chloro-8-hydroxyquinoline, 5-bromo-8-hydroxyquinoline, 5-bromo-7-chloro-8-hydroxyquinoline, 5,7-dibromo-8-hydroxyquinoline, 5-bromo-7-iodo-8-hydroxyquinoline, 7-bromo-8-hydroxyquinoline, 5-iodo-8-hydroxyquinoline, 5-iodo-7-chloro-8-hydroxyquinoline, 5,7-diiodo-8-hydroxyquinoline, 7-iodo-8-hydroxyquinoline, 5-sulfonic acid-8-hydroxyquinoline, 7-sulfonic acid-8-hydroxyquinoline, 5-sulfonic acid-7-iodo-8-hydroxyquinoline, 5-thiocyano-8-hydroxyquinoline, 5-chloro-8-hydroxyquinoline, 5-bromo-8-hydroxyquinoline, 5,7-dibromo-8-hydroxyquinoline, 5-iodo-8-hydroxyquinoline, 5,7-diiodo-8-hydroxyquinoline, 7-azaindole, 7-cyano-2-naphthol, 8-cyano-2-naphthol, 5-cyano-2-naphthol, 1-hydroxy-3,6,8-pyrenetrisulfonic acid, Trans-3-hydroxystilbene, 2-hydroxymethylphenol, or Pelargonidin.

Photoacid catalysts may include onium salts such as, for example, bis(4-tert-butylphenyl)iodonium perfluoro-1-butanesulfonate, diphenyliodonium perfluoro-1-butanesulfonate, diphenyliodonium-9,10-dimethoxyanthracene-2-sulfonate, diphenyliodonium hexafluorophosphate, diphenyliodonium nitrate, diphenyliodonium p-toluenesulfonate, diphenyliodonium triflate, (4-methylphenyl)diphenylsulfonium triflate, (4-methylthiophenyl)methyl phenyl sulfonium triflate, 2-naphthyl diphenylsulfonium triflate, (4-phenoxyphenyl)diphenylsulfonium triflate, (4-phenylthiophenyl)diphenylsulfonium triflate, thiobis(triphenyl sulfonium hexafluorophosphate), triarylsulfonium hexafluoroantimonate, triarylsulfonium hexafluorophosphate salt, triphenylsulfonium perfluoro-1-butanesulfonate, triphenylsulfonium triflate, tris(4-tert-butylphenyl)sulfonium perfluoro-1-butanesulfonate, tris(4-tert-butylphenyl)sulfonium triflate, bis(4-tert-butylphenyl)iodonium p-toluenesulfonate, bis(4-tert-butylphenyl)iodonium triflate, (4-bromophenyl)diphenylsulfonium triflate, (tert-butoxycarbonylmethoxynaphthyl)diphenylsulfonium triflate, (tert-butoxycarbonylmethoxyphenyl)diphenylsulfonium triflate, (4-tert-butylphenyl)diphenylsulfonium triflate, (4-chlorophenyl)diphenylsulfonium triflate, (4-fluorophenyl)diphenylsulfonium triflate, [4-[2-hydroxytetradecyl)oxy]phenyl]phenyliodonium hexafluoroantimonate, (4-iodophenyl)diphenylsulfonium triflate, (4-methoxyphenyl)diphenylsulfonium triflate, diphenyliodo hexafluorophosphate, diphenyliodo hexafluoroarsenate, diphenyliodo hexafluoroantimonate, diphenyl p-methoxyphenyl triflate, diphenyl p-toluenyl triflate, diphenyl p-isobutylphenyl triflate, diphenyl p-t-butylphenyl triflate, triphenylsulfonium hexafluorophosphate, triphenylsulfonium hexafluoroarsenate, triphenylsulfonium hexafluoroantimonate, triphenylsulfonium triflate, dibutylnaphthyl sulfonium triflate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)-sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluene sulfonate, tris(p-tert-butoxyphenyl)sulfonium p-toluenesulfonate, triphenylsulfonium nonafluorobutanesulfonate, triphenylsulfonium butanesulfonate, trimethyl-sulfonium trifluoromethanesulfonate, trimethylsulfonium p-toluenesulfonate, cyclohexylmethyl(2-oxocyclohexyl)-sulfonium trifluoromethanesulfonate, cyclohexylmethyl(2oxocyclohexyl)sulfonium p-toluenesulfonate, dimethylphenyl-sulfonium trifluoromethanesulfonate, dimethylphenyl-sulfonium p-toluenesulfonate, dicyclohexylphenylsulfonium trifluoromethanesulfonate, dicyclohexylphenylsulfonium p-toluenesulfonate, trinaphthylsulfonium trifluoromethane-sulfonate, cyclohexylmethyl(2-oxocyclohexyl)sulfonium trifluoromethanesulfonate, (2-norbornyl)methyl(2-oxocyclo-hexyl)sulfonium trifluoromethanesulfonate, ethylenebis[methyl(2-oxocyclopentyl)sulfonium trifluoromethane-sulfonate], or 1,2'-naphthylcarbonylmethyltetrahydrothiophenium triflate.

Photoacid catalysts may include diazomethane derivatives such as, for example, bis(benzenesulfonyl)-diazomethane, bis(p-toluenesulfonyl)diazomethane, bis(xylenesulfonyl)diazomethane, bis(cyclohexylsulfonyl)-diazomethane, bis(cyclopentylsulfonyl) diazomethane, bis(n-butylsulfonyl) diazomethane, bis(isobutylsulfonyl)-diazomethane, bis(sec-butylsulfonyl)diazomethane, bis(n-propylsulfonyl) diazomethane, bis(isopropylsulfonyl)-diazomethane, bis(tert-butylsulfonyl)diazomethane, bis(n-amylsulfonyl) diazomethane, bis(isoamylsulfonyl)-diazomethane, bis(sec-amylsulfonyl)diazomethane, bis(tert-amylsulfonyl) diazomethane, 1-cyclohexylsulfonyl-1-(tert-butyl sulfonyl) diazomethane, 1-cyclohexylsulfonyl-1-(tert-amylsulfonyl) diazomethane, or 1-tert-amylsulfonyl-1-(tert-butyl sulfonyl) diazomethane.

Photoacid catalysts may include glyoxime derivatives such as, for example, bis-o-(p-toluenesulfonyl)-α-dimethylglyoxime, bis-o-(p-toluenesulfonyl)-α-diphenylglyoxime, bis-o-(p-toluenesulfonyl)-α-dicyclohexyl-glyoxime, bis-o-(p-toluenesulfonyl)-2,3-pentanedione-glyoxime, bis-o-(p-toluenesulfonyl)-2-methyl-3,4-pentane-dioneglyoxime, bis-o-(n-butanesulfonyl)-α-dimethylglyoxime, bis-o-(n-butanesulfonyl)-α-diphenylglyoxime, bis-o-(n-butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluorooctanesulfonyl)-α-dimethylglyoxime, bis-o-(cyclohexane-sulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tertbutylbenzenesulfonyl)-α-dimethylglyoxime, bis-o-(xylenesulfonyl)-α-dimethyl-glyoxime, or bis-o-(camphorsulfonyl)-α-dimethylglyoxime.

Photoacid catalysts may include bissulfone derivatives such as, for example, bisnaphthylsulfonylmethane, bistrifluoromethylsulfonylmethane, Bismethylsulfonylmethane, bisethylsulfonylmethane, bispropylsulfonylmethane, bisisopropylsulfonylmethane, bis-p-toluenesulfonylmethane, bisbenzenesulfonylmethane, 2-cyclohexyl-carbonyl-2-(p-toluenesulfonyl)propane (β-ketosulfone derivative), 2-isopropylcarbonyl-2-(p-toluenesulfonyl) propane (β-ketosulfone derivative).

Photoacid catalysts may include disulfono derivatives such as, for example, diphenyl disulfone or dicyclohexyl disulfone.

Photoacid catalysts may include nitrobenzyl sulfonate derivatives such as, for example, 2,6-dinitrobenzyl p-toluenesulfonate or 2,4-dinitrobenzyl p-toluenesulfonate.

Photoacid catalysts may include sulfonic acid ester derivatives such as, for example, 1,2,3-tris(methanesulfonyloxy) benzene, 1,2,3-tris(trifluoro-methanesulfonyloxy)benzene, or 1,2,3-tris(p-toluenesulfonyloxy)benzene.

Photoacid catalysts may include sulfonic acid esters of N-hydroxyimides such as, for example, N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethyl-benzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethane-sulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxylmide methanesulfonate, N-hydroxy-5-norbornene-2,3-dicarboxylmide trifluoromethanesulfonate, N-hydroxy-5-norbornene-2,3-dicarboxylmide p-toluenesulfonate, N-hydroxynaphthalimide triflate, N-hydroxy-5-norbornene-2,3-dicarboximide perfluoro-1-butanesulfonate.

In certain embodiments, the photocatalyst is 8-hydroxyquinoline, which may act as a photoacid catalyst in lower pH solutions or as a photobase catalyst in higher pH solutions. In certain other embodiments, the photocatalyst is 8-hydroxy-1,3,6-pyrentrisulfonic acid trisodium salt (D&C Green 8). In various embodiments, the photocatalyst is a photobase. Photobase catalysts may include derivatives of trityl alcohols such as, for example, Malachite green. Photobase catalysts may also include acridine derivatives such as, for example, 9-hydroxy-10-methyl-9-phenyl-9,10-dihydroacridine. Photobase catalysts may also include photoactive carbamate-containing compounds.

The photocatalyst may be present in the compositions and methods described herein in an amount from 0.00050 percent to 30 percent by weight relative to the total weight of the composition. Generally, there is a preferred concentration of the photocatalyst. The preferred concentration of photocatalyst depends, in part, on a variety of factors including, for example, the chemical structure of the catalyst, the reaction medium, the reaction type, and the substrate.

Vehicle

The compositions described herein generally include a vehicle suitable for dispersing or dissolving the active material, the photocatalyst, and any other components to facilitate application of the composition onto the substrate surface or into the bulk portions of the substrate. The vehicle may comprise one or more of a solvent, an emulsifier, a surfactant, or other dispersant. The vehicle may also be a physiologically acceptable vehicle. The properties of a suitable vehicle are dependant, at least in part, on the properties of the other components of the composition and the substrate to be modified.

A suitable vehicle operates to disperse or dissolve the active material, the photocatalyst, and any other components, and to facilitate application of the composition onto the substrate surface. A suitable vehicle facilitates sufficient contact between the active material and the substrate. In various embodiments, a physiologically acceptable vehicle may be any carrier, solvent, or solvent-containing composition that is suitable for application to physiological tissues such as human hair and human skin, for example. In various embodiments, a physiologically acceptable vehicle is a cosmetically or dermatologically acceptable carrier.

A suitable vehicle may be a solvent. In personal and consumer care product applications, for example, water is a useful solvent. In various embodiments, the compositions described herein may include water in an amount from 1% to 98% by weight relative to the total weight of the composition. Water is also a physiologically acceptable vehicle. Additional solvent or solvent-containing physiologically acceptable vehicles include, but are not limited to, hydroxyl-containing liquids (e.g., alcohols), silicones, oils, hydrocarbons, glycols, ammonium lauryl sulfate, sodium lauryl sulfate, and combinations thereof. In certain embodiments, for example, where the active material is at least partially insoluble in water, other solvents, dispersants, or emulsifiers may be used as physiologically acceptable vehicles, alone or in combination with each other and/or with water.

A suitable vehicle is therefore generally used to dilute and/or emulsify the components forming the compositions described herein. A suitable vehicle may dissolve a component (true solution or micellar solution) or a component may be dispersed throughout the vehicle (suspension, dispersion or emulsion). The vehicle of suspension, dispersion or emulsion is typically the continuous phase thereof. That is, other components of the suspension, dispersion or emulsion are distributed on a molecular level or as discrete or agglomerated particles throughout the vehicle. The preparation of such emulsions or dispersions of the active in these cases may be highly important. Small particles contribute to an intimate contact between the active, the substrate and the photoacid catalyst, increasing the reaction rate. For example, in the case of hair surface modification using fatty alcohol and 8-hydroxyquinoline in a water medium, an emulsion that contains very small particles (for example, less than 500 nanometers or more preferably less than 200 nanometers) may be substantially more effective in providing a durable hydrophobic surface than an emulsion containing larger particles (for example, see the data in FIG. 7 corresponding to Examples 4 versus 4A).

It will be readily apparent to one of ordinary skill in the art that the appropriate vehicle(s) are dependent upon the specific active material(s), photocatalyst(s), and other optional component(s) used in the compositions described herein.

Optional Components

The compositions and methods described herein may optionally include a variety of components. For example, in various embodiments, the compositions and methods described herein may include surfactants, emulsifiers, oxidants, reductants, pH regulators, emollients, humectants, proteins, peptides, amino acids, additive polymers, glossers, oils and/or fatty acids, lubricants, sequestrants/chelators, antistatic agents, rheology modifiers, feel agents, fillers, dyes, preservatives, perfumes, other functional components, or combinations thereof. Particular optional components may be found in the CTFA International Cosmetic Ingredient Dictionary, Tenth Edition, 2004; and in McCutcheon, Detergents and Emulsifiers, North American Edition (1986). It will be readily apparent to one of ordinary skill in the art that the particular optional components utilized will be dependant, at least in part, upon the specific applications for the compositions and methods.

In various embodiments, the compositions and methods described herein include an oxidizing agent (oxidant). An oxidant may be added, for example, to render a substrate surface more amenable to photocatalytic covalent modification/functionalization in accordance with the various embodiments described herein. An oxidant may be present in an amount form 0.00050% to 25% by weight relative to the total weight of the composition. Suitable oxidants include, for example, one or more of hydrogen peroxide, urea peroxide, melamine peroxide, percarbonates, alkali metal bromates, perborates, bromates, hypochlorites, chlorites, perchlorates, iodates, periodates, permanganates and persulfates. In certain embodiments, the oxidant is hydrogen peroxide.

The identity of the reaction system, the quantities and concentrations of reagents utilized, and the reaction conditions are all dependent, at least in part, upon the substrate to be modified, the active material utilized, and the manner in which the active material is to be associated with the substrate. These considerations are readily determinable by one of ordinary skill in the art in practice of the compositions and methods described herein.

EXAMPLES

The following examples are intended to more clearly illustrate aspects of the compositions and methods described herein, but are not intended to limit the scope thereof.

Example 1A

Preparation of Prototype Silicone Emulsion 1A

Into a 500-mL beaker containing 200 mL of tetrahydrofuran 6.0 grams of silicone polymer (Dow Corning® 5562 Carbinol Fluid) are added and dissolved with mild mixing. Into this solution, 200 mL of water are added dropwise (over 15 minutes) under high shear mixing using a Silverson® L4RT homogenizer at 6000 rpm. The resulting emulsion is continuously mixed under high shear for 2 more hours. Then, 0.030 grams of 8-hydroxyquinoline are added and the composition is stirred for 10 minutes.

Example 1B

Preparation of Prototype Silicone Emulsion 1B

The procedure of Example 1A is repeated replacing the silicone polymer Dow Corning® 5562 Fluid with Momentive® Silicone Polymer Baysilone OF OH 702E.

Example 2A

Hair Treatment by Dipping in Prototype Silicone Emulsion 1A

A 20 cm long (4.0-gram) hair switch is oxidized with bleach solution, washed and air dried. In a dark room, the hair switch is dipped into a beaker containing 100.0 g of the emulsion from Example 1A. The hair switch is removed from the beaker after 15 minutes and exposed to a bright light (Aquarium 20W Fluorescent tube AquaRays® Model No F20WT12-AR-FS) for 15 minute. The hair switch is then rinsed with a 100 mL of methyl isobutyl ketone/toluene (1:1) 3 times and then dipped into a fresh solution of 250 mL of this solvent mixture for 30 minutes, and then hanged to air dry. After drying, it is washed with clarifying shampoo (Pantene Pro-V® Clarifying Shampoo), thoroughly rinsed with running tap water for 3.0 minutes, and air dried for at least 5 hours. The washing/rinsing is repeated 3 times. The procedure is repeated with two more identical hair switches (from the same lot).

Example 2B

Hair Treatment by Dipping in Prototype Silicone Emulsion 1B

The procedure of Example 2A is repeated, replacing Prototype Silicone Emulsion 1A with Prototype Silicone Emulsion 1B.

The various embodiments of the compositions and methods described herein are primarily discussed in connection with hair, skin and fabric substrates. Nevertheless, it is recognized that the invention set forth in the following claims is not limited in application to any particular substrate. The invention set forth in the following claims may be used in connection with any substrate for which it is useful to treat the surface with the compositions and methods described herein as recognizable by one of ordinary skill in the art. Non-limiting examples of such substrates include, for example, fabric, paper, wood, plastic, glass, tile, stone, concrete, brick, other ceramics, and composites.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   (a) an active material having one or more functional groups capable of covalent attachment in the presence of an acid or a base to one or more complementary functional groups; wherein the active material is selected from the group consisting of Bis-Hydroxyethoxypropyl Dimethicone, and a silicone copolymer from monomers which contain organic alcohol groups having the structure:

R1-[Si(CH2)(R3-CH2OH)—O]$n$-[Si(CH2)2-O]$m$-R2 wherein R1 and R2 are methyl; and R3 is CH2CH2CH2-(OCH2CH2O)q-H with q≧1; and
   (b) a photocatalyst capable of generating an acid or a base upon exposure to light; wherein said photocatalyst is a photoacid or photobase selected from the group consisting of aromatic hydroxyl compounds, sulfonated pyrene compounds, onium salts, diazomethane derivatives, bis-sulfone derivatives, disulfuno derivatives, nitrobenzyl sulfonate derivatives, sulfonic acid ester derivatives, sulfonic acid esters of N-hydroxyimides, and combinations thereof wherein the light absorbed by the photocatalyst is selected from the group consisting of ultraviolet light, visible light, and combinations thereof and
   (c) a physiological acceptable vehicle for dispersing or dissolving the active material and the photocatalyst for application of the composition to a substrate; and wherein the vehicle is a physiological acceptable vehicle and the substrate is selected from the group consisting of hair, skin, nail, teeth and combinations thereof.

2. The composition of claim 1, wherein the active has a molecular weight greater than 50,000 grams/mole.

3. The composition recited in claim 1 further comprising a component selected from the group consisting of a surfactant, an emulsifier, an oxidant, a pH controlling component, a feel agent, a rheology modifier, a filler, a perfume, and combinations thereof.

4. The composition recited in claim 1 wherein the vehicle comprises a solvent.

5. The composition recited in claim 1 wherein the vehicle is selected from the group consisting of water, silicones, oils, hydrocarbons, lauryl sulfate salts and combinations thereof.

6. The composition recited in claim 1 wherein the photoacid is an aromatic hydroxyl compound.

7. The composition recited in claim 6 wherein the aromatic hydroxy compound is a hydroxyl-substituted quinoline.

8. The composition recited in claim 7 wherein the hydroxyl-substituted quinoline is 8-hydroxyquinoline.

9. The composition recited in claim 1 wherein the aromatic hydroxyl compounds are selected from the group consisting of hydroxyl-substituted quinolines, trityl alcohol derivatives and acridine derivatives.

10. The composition recited in claim 9 wherein the photobase is a hydroxyl-substituted quinoline.

11. The composition recited in claim 10 wherein the photobase is 8-hydroxyquinoline.

12. The composition recited in claim 9 wherein the photobase is Malachite green.

13. The composition recited in claim 9 wherein the photobase is 9-hydroxy-10-methyl-9-phenyl-9,10-dihydroacridine.

14. The composition recited in claim 1 wherein the personal care composition is selected from the group consisting of lipstick, mascara, rouge, foundation, blush, eyeliner, lipliner, lip gloss, body powder, sunscreen, sun block, nail polish, mousse, spray, styling gel, nail conditioner, bath gel, shower gel, shampoo, cream rinse, hair dye, hair coloring product, hair conditioner, hair shine product, hair anti-frizz product, malodor absorber/remover, lip balm, skin conditioner, cold cream, moisturizer, hair spray, soap, body scrub, exfoliant, astringent, depilatory, permanent waving solution, antidandruff formulation, antiperspirant composition, deodorant, shaving product, preshaving product, after shaving product, cleanser, skin gel, and rinse.

15. The composition recited in claim 1 wherein the photocatalyst is present in an amount from 0.00050% to 10% by weight relative to the total weight of the composition.

16. The composition recited in claim 1, wherein the active material comprises Bis-Hydroxyethoxypropyl Dimethicone, the photocatalyst comprises 8-hydroxyquinoline, the vehicle comprises sodium lauryl sulfate, and the composition further comprises water and hydrogen peroxide.

17. A method for treating a substrate comprising:
    a) applying at least one active material to the substrate, the active material having one or more functional groups, and the substrate having one or more complementary functional groups; wherein the active material is selected from the group consisting of Bis-Hydroxyethoxypropyl Dimethicone, and a silicone copolymer from monomers which contain organic alcohol groups having the structure:

R1-[Si(CH2)(R3-CH2OH)—O]$n$-[Si(CH2)2-O]$m$-R2 wherein R1 and R2 are methyl; and R3 is CH2CH2CH2-(OCH2CH2O)q-H with q≧1; and
    b) applying to the substrate at least one photocatalyst capable of generating an acid or base on exposure to light; wherein said photocatalyst is a photoacid or photobase selected from the group consisting of aromatic hydroxyl compounds, sulfonated pyrene compounds, onium salts, diazomethane derivatives, bis-sulfone derivatives, disulfuno derivatives, nitrobenzyl sulfonate derivatives, sulfonic acid ester derivatives, sulfonic acid esters of N-hydroxyimides, and combinations thereof wherein the light absorbed by the photocatalyst is selected from the group consisting of ultraviolet light, visible light, and combinations thereof; and
    c) exposing the photocatalyst and the at least one active material to light for forming covalent attachments between the one or more functional groups of the at least one active material and a reagent selected from the group consisting of a second active material, a substrate and a combination thereof.

18. The method of claim 17, wherein the covalent attachment is between the one or more functional groups of the at least one active material and a second active material to form a product.

19. The method of claim 18, wherein the product is further reacted with a substrate.

20. The method of claim 18, wherein the covalent attachments is an esterification reaction between the one or more functional groups of the at least one active material and the substrate.

21. The composition recited in claim 1, wherein the active material comprises silicone copolymer from monomers which contain organic alcohol groups having the structure:

R1-[Si(CH2)(R3-CH2OH)—O]$n$-[Si(CH2)2-O]$m$-R2 wherein R1 and R2 are methyl; and R3 is CH2CH2CH2-(OCH2CH2O)q-H with q≧1;
    the photocatalyst comprises 8-hydroxyquinoline, the vehicle comprises sodium lauryl sulfate, and the composition further comprises water and hydrogen peroxide.

* * * * *